United States Patent [19]
Pesenti et al.

[11] Patent Number: 5,224,472
[45] Date of Patent: Jul. 6, 1993

[54] INHALATION DEVICE

[75] Inventors: Yvan Pesenti, Grenoble; Jean-Philippe Quenderff, Meyland, both of France

[73] Assignee: Solange Quenderff, Meylan, France

[21] Appl. No.: 652,513

[22] Filed: Feb. 8, 1991

[30] Foreign Application Priority Data

Feb. 9, 1990 [FR] France ............... 90 01928

[51] Int. Cl.⁵ ............................................. A61M 11/00
[52] U.S. Cl. ........................ 128/200.23; 128/200.14
[58] Field of Search ................ 128/200.14, 200.23

[56] References Cited

U.S. PATENT DOCUMENTS

| | | | |
|---|---|---|---|
| 3,157,179 | 11/1964 | Paullus et al. | 128/211 |
| 3,456,645 | 7/1969 | Brock | 128/173 |
| 3,456,646 | 7/1969 | Phillips et al. | 128/173 |
| 3,565,070 | 2/1971 | Hanson et al. | 128/173 |
| 3,598,294 | 8/1971 | Hedrick et al. | 222/402.2 |
| 3,605,738 | 9/1971 | Ciranna | 128/173 |
| 3,636,949 | 1/1972 | Kropp | 128/173 R |
| 3,789,843 | 2/1974 | Armstrong et al. | 128/173 |
| 3,814,297 | 6/1974 | Warren | 222/402.13 |
| 3,826,413 | 7/1974 | Warren | 222/402.13 |
| 4,414,972 | 11/1983 | Young et al. | 128/200.23 |
| 4,592,348 | 7/1986 | Water, IV et al. | 128/200.23 |
| 4,648,393 | 3/1987 | Landis et al. | 128/200.23 |
| 4,664,107 | 5/1987 | Wass | 128/200.23 |
| 4,803,978 | 2/1989 | Johnson, IV et al. | 128/200.23 |

FOREIGN PATENT DOCUMENTS

| | | |
|---|---|---|
| 0232235 | 8/1987 | European Pat. Off. |
| 040641 | 5/1982 | Fed. Rep. of Germany |
| 82/01133 | 4/1982 | PCT Int'l Appl. |
| 1269554 | 4/1972 | United Kingdom |
| 1269811 | 4/1972 | United Kingdom |
| 1335378 | 10/1973 | United Kingdom |
| 1383761 | 2/1975 | United Kingdom |
| 2204799 | 5/1987 | United Kingdom |
| 2233236 | 6/1989 | United Kingdom |

Primary Examiner—Edgar S. Burr
Assistant Examiner—Aaron J. Lewis

[57] ABSTRACT

An inhalation device is provided for use with an aerosol container having a body portion and a discharge stem movable with respect to the body portion from a rest position in which discharge is prevented to an operative position in which discharge takes place. The device has a housing for the inhalation device, and an outlet provided in the housing through which a patient can inhale. A restraining and pressure-sensing member is provided in the form of a resiliently flexible plate. The plate has a first position in which it prevents relative movement between the discharge stem and the body portion to the operative position and a second position in which it permits such movement. The plate senses when a reduced pressure is produced through inhalation by the patient and moves from the first position to the second position in response thereto.

16 Claims, 6 Drawing Sheets

INHALATION DEVICE

FIELD OF THE INVENTION

This invention relates to an inhalation device for use in enabling material in aerosol form to be dispensed from a container. The invention is particularly concerned with a metered dose inhalation device by means of which a metered amount of a medicament-containing liquid can be dispensed to a patient in aerosol form.

BACKGROUND OF THE INVENTION

Metered dose inhalers are well known in medicine for the treatment of, or alleviation of the effects of, respiratory complaints, for example asthma. The medicament-containing liquid is held under pressure in a container which is mounted, usually removably, in an inhalation device. The aerosol container has a body portion, and a discharge stem movable with respect to the body portion from an inoperative position in which discharge is prevented to an operative position in which discharge takes place. To operate the inhalation device the patient needs to cause relative movement to take place between the body portion of the aerosol container and the discharge stem, for example by pressing on the closed end of the body portion, and this must be coordinated with inhalation on the part of the patient. Unfortunately, many patients needing this type of treatment are unable to coordinate their breathing with manual actuation of the device.

To try to overcome this problem devices have been proposed in which the act of inhalation itself causes the device to deliver a dose of medicament. Such devices are known as breath-actuated devices.

In designing a breath-actuated inhalation device there are a number of requirements which must be met but which are difficult to reconcile with one another. Thus, a substantial force is needed to move the body portion and discharge stem with respect to one another, but only a small force can be produced by inhalation, particularly in the case of the patients most likely to be using the device, which are persons having breathing difficulties. It has been proposed to overcome this problem by providing the inhalation device with an auxiliary energy store, for example in the form of a spring, the spring tending to cause the device to discharge a dose and being restrained from doing so by some form of restraining mechanism. The small force produced by inhalation is then used to release the restraining mechanism and permit the spring to operate the device.

However, this in turn gives rise to a further problem, which is that of maintaining the stability of the device. If the restraining mechanism can be released by the small force generated through inhalation then there is a risk that it may also be released accidentally when inhalation is not taking place. Conversely, if the restraining mechanism is held in place sufficiently securely to prevent accidental release, the force which a patient can generate by inhalation may be insufficient to release it.

BRIEF SUMMARY OF THIS INVENTION

The present invention aims to provide an inhalation device which addresses these conflicting requirements and provides a workable solution.

According to the invention there is provided an inhalation device for use with an aerosol container having a body portion and a discharge stem movable with respect to the body portion from a rest position in which discharge is prevented to an operative position in which discharge takes place, the device comprising a housing for the inhalation device, an outlet provided in the housing through which a patient can inhale, and a restraining and pressure-sensing member having a first position in which it prevents relative movement between the discharge stem and the body portion to the operative position and a second position in which it permits such movement, the said member sensing when a reduced pressure is produced through inhalation by the patient and moving from the first position to the second position in response thereto.

In a preferred embodiment of the invention the member referred to as the restraining member or restraining and pressure-sensing member takes the form of a resiliently flexible plate, for example of metal such as steel. Alternatively, it is possible to use a pair of plates, which need not be resiliently flexible, which are hinged together. One possible way of achieving this is for the pair of plates and the hinge to be integral with one another, for example with the hinge being a so-called "living" hinge. A similar effect may be achieved using a single plate which is reduced in thickness along a transversely extending line to such an extent that the portion of reduced thickness forms, in effect, a hinge axis.

BRIEF DESCRIPTION OF THE DRAWINGS

A number of embodiments of the invention will now be described with reference to the accompanying drawings, in which.

DETAILED DESCRIPTION OF PREFERRED EMBODIMENTS

Figure 1:
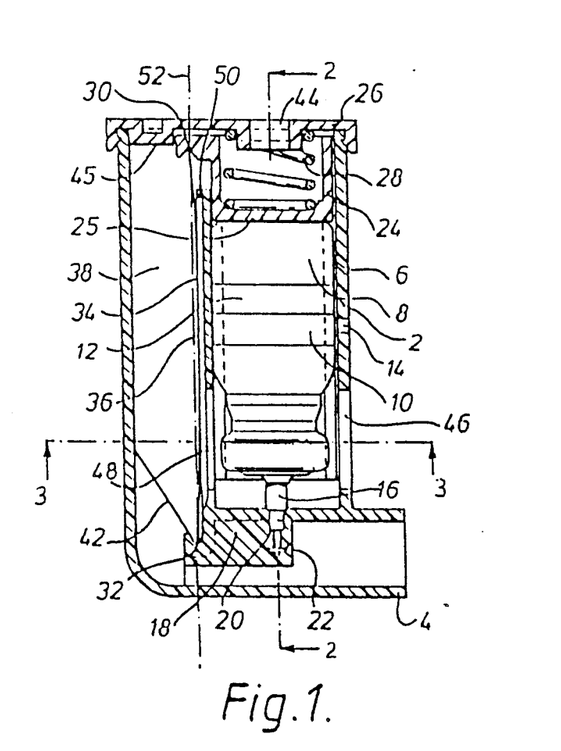
FIG. 1 shows a first embodiment, and is a vertical section taken on line A—A in FIG. 2.
Figure 2:
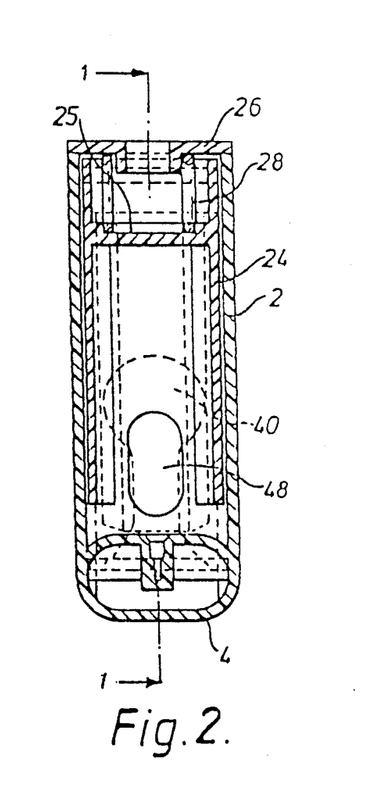
FIG. 2 shows the first embodiment and is a vertical section taken on line B—B in FIG. 1.
Figure 3:
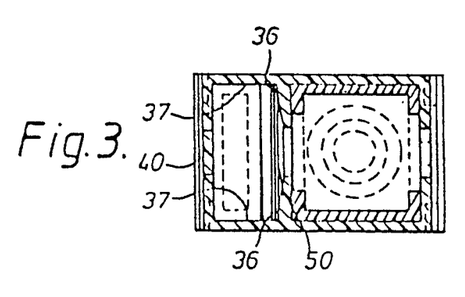
FIG. 3 is a cross-section taken on line C—C in FIG. 1.
Figure 4:
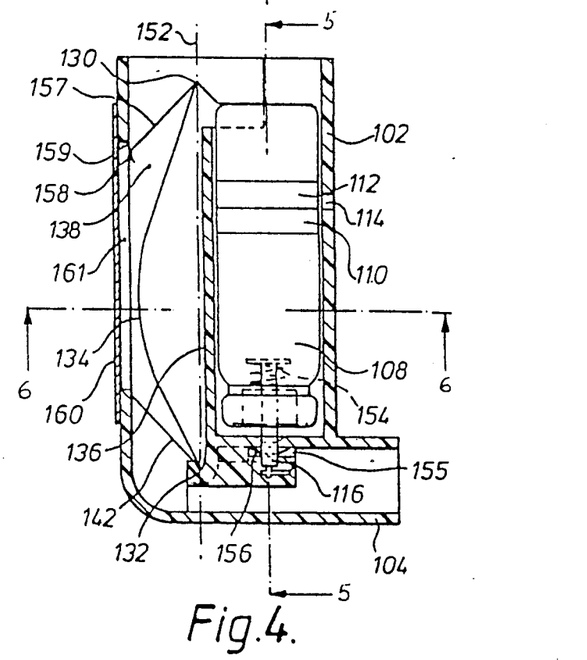
FIG. 4 shows a second embodiment of the invention and is a vertical section taken on line A—A in FIG. 5.
Figure 5:
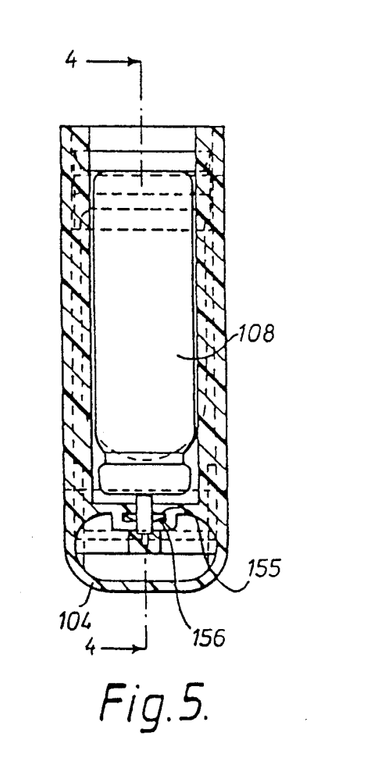
FIG. 5 is a vertical section taken on line B—B in FIG. 4.
Figure 6:
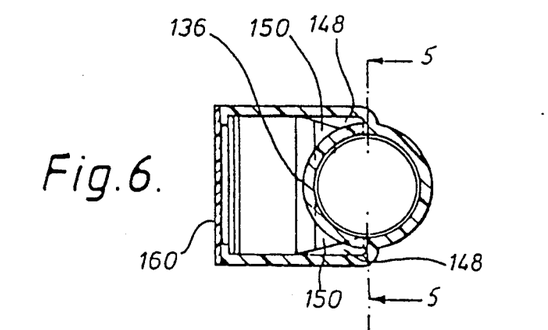
FIG. 6 is a section taken on line C—C in FIG. 4.
Figure 7:
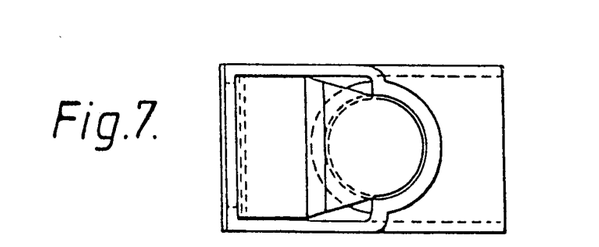
FIG. 7 is a top plan view of the embodiment of FIGS. 4 to 6.

Referring now to the first embodiment, shown in FIGS. 1 to 3, this comprises a housing 2 provided with an integral outlet spout 4. This is shown in the form of a mouthpiece, and will be so referred to below, but it could alternatively be in the form of a nose piece. Within the housing 2 there is defined a compartment 6 within which the body portion of an aerosol container 8 is received. The compartment 6 is slightly longer than the body portion of the aerosol container, and the body portion is longitudinally slidable within the compartment. The body portion carries indicia, for example in the form of coloured stripes 10 and 12 which may, for example, be coloured green and red respectively. One or other of these stripes is visible through an aperture 14 in the front wall of the housing 2, depending on the longitudinal position of the body portion of the aerosol container.

The aerosol container has a discharge stem 16 extending from the body portion in conventional manner, and the end of this is received in a opening in a stem block 18 formed integrally within the mouthpiece 4. The opening is chamfered where the discharge stem enters it, to make the discharge stem easier to insert. The distal end of the discharge stem bears against a shoulder 20, and the outlet of the discharge stem communicates with a discharge orifice 22. In conventional manner, the discharge stem is biassed outwardly with respect to the body portion by a spring (not shown) within the container.

A guide 24 is longitudinally slidable in the compartment 6. As can be seen most clearly in FIG. 2 this has the general shape of an H, as viewed in longitudinal section. The guide has a transverse wall 25. The upper end of the housing 2 is closed by a cover 26, and a compression spring 28 is mounted between the transverse wall 25 of the guide 24 and the cover 26, to urge the guide, and hence the body portion of the aerosol container 8, in a downward direction. The cover is preferably removable to allow a container, when empty to be replaced by a fresh one.

A downwardly facing groove 30 is formed in the guide 24, and an upwardly facing groove 32 is formed in the stem block 18. The upper and lower edges of a resiliently flexible plate 34 are received in the grooves 30 and 32 respectively. This plate may suitably be made of steel a few hundredths of a millimetre thick, though other materials might be used instead. In an unstressed condition the plate 34 is substantially planar. In the position shown in FIGS. 1 to 3, which is referred to below as the cocked position, the plate 34 is slightly curved and the portion centrally of its length is urged against walls 36 under the force applied to the plate by the spring 28. The lateral edges of the plate 34 are closely adjacent the side walls 37 of the housing 2, but with sufficient play to allow easy movement of the plate in a manner described further below.

A chamber 38 is defined between the plate 34 and the rear wall of the housing 2. A keyhole-shaped cut is made in the rear wall of the housing to define a correspondingly keyhole-shaped tab 40. The width of the cut is chosen with a view to achieving an appropriate rate at which air can leak into the chamber 38 to assist delivery of the dose of medicament. The tab remains attached to the rest of the wall at its lower end, and the material of the rear wall, at least where the tab is attached, is sufficiently flexible to allow the tab to be pushed inwardly, and is sufficiently resilient to cause the tab to spring back to its original position when a force is no longer applied. FIG. 1 also shows one of the two ribs 42 with which the side walls of the chamber 38 are provided and which help to guide the lower edge of the plate 34 into the groove 32 during assembly.

It will be noted that the device is provided with a number of further openings, in addition to those already described. Thus, the cover 26 is provided with a vent 44 to keep the portion of the guide 24 above the transverse wall 25 at atmospheric pressure. The vent 44 also serves to provide air to the chamber 38 after the upper end of the guide 24 has passed below the lower face 45 of the cover 26, for inhalation with the medicament by the patient. The front wall of the housing 2 is provided with a vent 46 which maintains the compartment 6 at atmospheric pressure. This atmospheric pressure is further communicated by a vent 48 to the front face of the plate 34. This is facilitated by the provision of a small longitudinal chamber 50.

The way in which the device described above operates is as follows. Assume that the device is in the position shown in FIGS. 1 to 3, i.e. it is in the cocked position. This is indicated to the patient by the fact that the green stripe 10 is visible through the aperture 14. The patient inhales through the mouthpiece, and this causes the pressure in chamber 38 to be reduced to a level below atmospheric pressure. The front surface of the plate 34 is at atmospheric pressure, and this pressure differential causes the plate 34 to try to move rearwardly. Since the upper and lower edges of the plate are held in the grooves 30 and 32, the result is that the plate first moves to a straight condition, as indicated by the line 52. In so doing it forces the guide 24 slightly upwards against the force of the spring 28. It will be seen that in the cocked position there is a small gap between the upper end of the guide 24 and the lower surface of the cover 26, to permit this movement. The amount by which the plate deviates in its cocked position from the line 52 determines the amount which will have to be done by the plate in order to reach the straight condition. Typically the deviation of the plate at its centre is of the order of a few tenths of a millimetre. The shorter the distance, the more sensitive the device.

The plate then moves past the straight condition into a condition in which it is curved in the opposite direction to that shown in the drawing. Once past its straight condition the plate is free to curve to a substantial degree, and as it does so the guide 24 is free to move downwardly under the force of the compression spring 28. This causes the body of the aerosol container 8 to move downwardly, whilst the discharge stem remains fixed in the stem block 18, and this relative movement between the body and the stem causes a metered dose to be discharged through the discharge stem and thence through the outlet orifice 22 and mouthpiece 4 to the patient. The red stripe 12 is then visible through the aperture 14. It will be appreciated that the spring 28 must be sufficiently strong to overcome the force which normally biases the metering stem outwardly with respect to the aerosol container, and also to overcome frictional forces acting to resist longitudinal sliding of the aerosol container and the force exerted by the plate 34 as it bends.

After the patient has received a dose the device can be returned to its cocked position, and it is desirable that this should be done immediately following use. To achieve this the patient presses on the tab 40, which flexes inwardly and urges the plate 34 back past its straight position into the position shown in the drawings. In doing so the guide 24 is caused to travel upwards, thus re-compressing the spring 28.

The second embodiment, shown in FIGS. 4 to 7, will now be described. Elements in this embodiment which correspond substantially to elements in the first embodiment are represented using the same reference numerals but with the addition of 100.

This second embodiment has no external spring corresponding to the spring 28 used in the first embodiment, and hence no guide 24. Instead, it uses a modified aerosol container in which the discharge stem 116, instead of being urged outwardly by an internal spring (as is conventional) is urged inwardly. The spring which achieves this is shown diagrammatically in FIG. 4, where it is represented by reference numeral 154. Thus, in the second embodiment the spring 154 provides the potential energy store which is provided by spring 28 in the first embodiment. In view of the fact that no guide is provided corresponding to guide 24 in the first embodiment, the body portion of the aerosol container 110 used in the second embodiment is more elongated so as to improve the accuracy with which it slides. A chamber 155 is formed in the stem block, and this receives a conical washer 156 which grips the discharge stem 116 and prevents it moving upwardly under the force of the compression spring 154.

The groove for receiving the lower edge of the flexible plate, the groove here being denoted by reference numeral 132, is formed, as in the first embodiment, in the stem block. However, since there is no guide in the second embodiment the upper groove, here denoted by reference numeral 130, is formed instead by providing the aerosol container with an integral plate 157 which is folded to define the groove 130. The plate 157 also performs a further function, namely to close the upper end of the chamber 138 when the device is in its cocked position. For this purpose the distal end of the plate 157 is curved to form a slide 158 which runs against the rear wall of the chamber 138. The second embodiment is shown in FIGS. 4 to 7 in the position which it occupies as a dose is being discharged, and it will be seen that by the time this position is reached the slide 158 has moved downwards to a position such that it no longer closes the chamber 138, air being free to flow through the gap 159 into that chamber.

One other respect in which the second embodiment differs from the first embodiment is in the way in which the device is re-cocked. Instead of the tab 40 used in the first embodiment, an aperture 161 is provided in the rear wall of the housing and this is covered by an air-impermeable deformable membrane 160 the edges of which are adhered, or otherwise secured, to the surrounding part of the housing. To re-cock the device, the patient pushes on the membrane 161 so that it comes into contact with the plate 134, and continues to push to cause the plate to go past its straight condition into engagement with the face 136.

Figure 8:
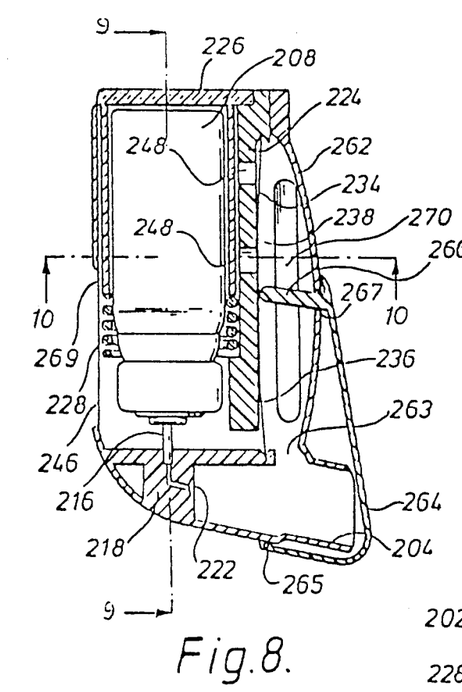
FIG. 8 shows a third embodiment of the invention and is a vertical section taken on line A—A in FIG. 9.
Figure 9:
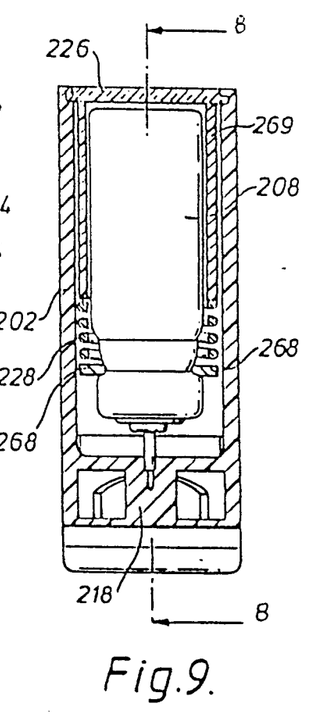
FIG. 9 is a vertical section taken on line B—B in FIG. 8.
Figure 10:
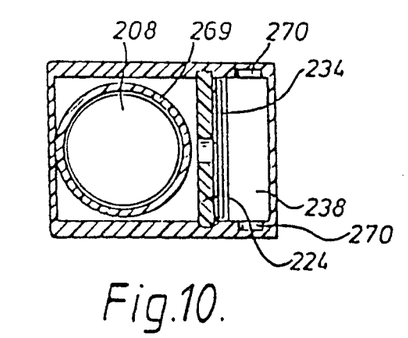
FIG. 10 is a cross-section taken on line C—C in FIG. 8.
Figure 11:
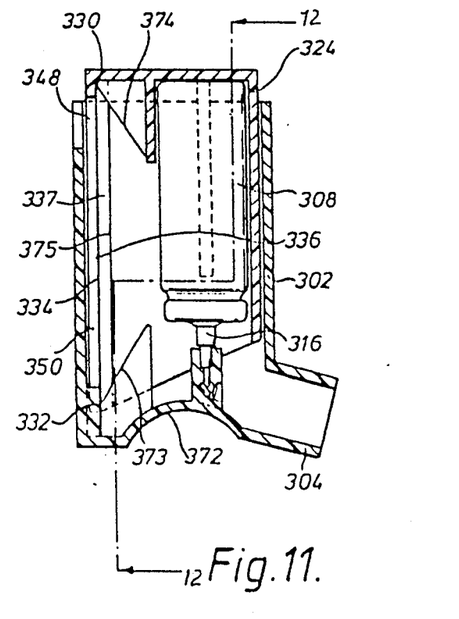
FIG. 11 shows a fourth embodiment of the invention and is a vertical section taken on line A—A in FIG. 12.
Figure 12:
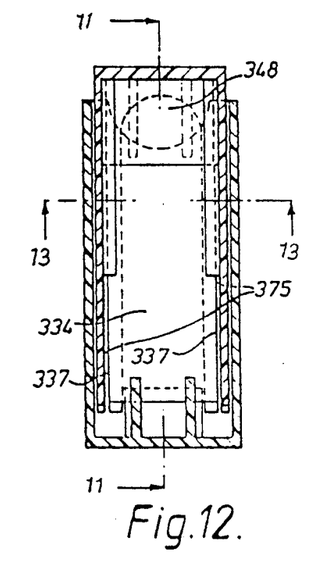
FIG. 12 is a section taken on line B—B in FIG. 11.
Figure 13:
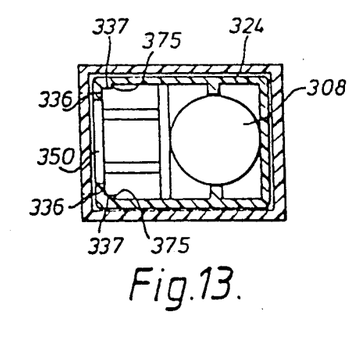
FIG. 13 is a cross-section taken on line C—C in FIG. 12.

The third embodiment, shown in FIGS. 8 to 10, resembles in a number of respects the first embodiment, and corresponding elements are denoted by corresponding numerals, but with the addition of 200. As in the case of the first embodiment, the third embodiment uses a conventional aerosol container in which the discharge stem is biassed outwardly with respect to the body portion of the container.

It will be seen that in the embodiment of FIGS. 8 to 10 the resiliently flexible plate, here denoted by reference numeral 234, is at the front of the device, rather than at the rear as in the first embodiment. The chamber 238 is defined between the plate 234 and a front wall 262, and an opening 263 provides communication between the mouthpiece 204 and the chamber 238 to allow a sub-atmospheric pressure to be produced in the chamber 238 when the user inhales. The mouthpiece is provided with a cover 264 which is hinged to the mouthpiece at pivot 265 and which carries a post 266 which is integral with the cover adjacent the distal end thereof. When the cover is closed, as it is in FIGS. 8 to 10, the post 266 extends through an opening 267 in the front wall 262, so that the tip of the post bears against the plate 234 to urge it into contact with the adjacent wall 236. The size of the opening 267 should be so chosen that the flow of air which passes in through the opening during inhalation is at an acceptable level. It is desirable for some air to enter in this way so that the resistance to inhalation experienced by the patient is not too great. On the other hand, the amount must not be so great that the pressure reduction in the chamber 238 is inadequate to move the plate 234 rightwardly. Preferably, the device should operate when the patient is inhaling at a rate of about 30 l/min.

The can 208 is gripped by arms 268 which are integral with the guide 224. The upper portion of the body of the aerosol container is surrounded by a tube 269, and the spring 228 is compressed between the tube 269 and the arms 268 to urge the body portion of the container downwardly.

When the device is in the position shown in FIGS. 8 to 9, the guide 224, and hence the body portion of the container 208, are unable to move under the urging of the spring 228, by virtue of the presence of the plate 234. When the patient desires to use the device he opens the cover 264, thus bringing the post 266 out of contact with the plate 234. The plate 234 remains in the illustrated position until the patient inhales through the mouthpiece 204, at which point the reduced pressure created in the chamber 238 causes the plate 234 to flex rightwardly, allowing the guide 224 to move downwardly carrying the body portion of the container with it by virtue of the arms 268. A dose of medicament is thus delivered to the patient. After use, the patient recloses the cover 264, in the course of which the post 266 pushes the plate 234 back into the position shown in the drawings, so that the device is re-cocked ready for subsequent use.

To assist in providing air to the patient during inhalation, a pair of channels 270 are provided in the side walls of the chamber 238.

The three embodiments thus far described operate automatically, in the sense that the act of inhalation itself causes a dose to be delivered. The fourth embodiment, which is shown in FIGS. 11 to 14 is manually operated, and the act of inhalation permits, but does not itself cause, a dose to be delivered. Elements in this embodiment which correspond generally to elements in the first embodiment are denoted by the same reference numerals but with the addition of 300.

In the fourth embodiment relative movement between the body portion and discharge stem of the aerosol container is produced manually by the patient. To achieve this the patient presses the guide 324 inwardly with respect to the housing 302, and to make it easier for the patient to grasp the device whilst doing so the housing is provided with a depression 372 adjacent the stem block. However, unless the patient simultaneously inhales while attempting manual operation no relative movement between the guide 324 and the housing 302 can take place because of the presence of the plate 334. In this embodiment, unlike the preceding embodiments, the plate is planar when the device in its cocked position, and to ensure that it stays in its correct position while the device is cocked it is pre-curved so that its natural tendency is to bow leftwardly as viewed in FIGS. 11 and 13. It is prevented from doing this by the walls 336, and thus presses against these walls with a force dependent on the degree of pre-curvature which has been applied. To assist in installing the plate 334 ribs 373 and 374 are formed on the interior of the housing 302 and guide 324.

Figure 14:
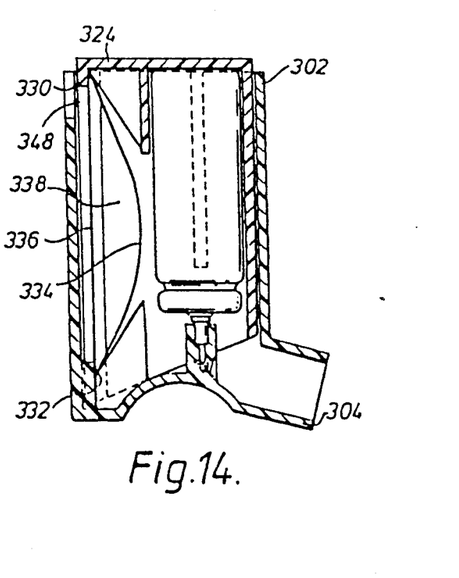
FIG. 14 corresponds to FIG. 11, but shows the device in a different position.

When the patient inhales a sub-atmospheric pressure is applied to the front of the plate 334, which therefore bows rightwardly, permitting manual force on the slide 324 to move it inwardly with respect to the housing 302. This is shown in FIG. 14. Once the centre part of the plate 334 moves past ribs 375 which are formed on the interior of the guide 324, air is free to flow into the interior of the device to the mouthpiece 304 via the vent 348 and the longitudinal chamber 350 and around the longitudinal edges of the plate 334.

After use, the device is automatically re-cocked. This is achieved because when the patient releases pressure on the guide 324, the body portion of the aerosol container is able to move to its original position under the force of the spring within the aerosol valve. This moves the guide 324 back to its original position. At the same time, the energy stored in the plate 334 helps to restore the guide to its original position.

Figure 15:
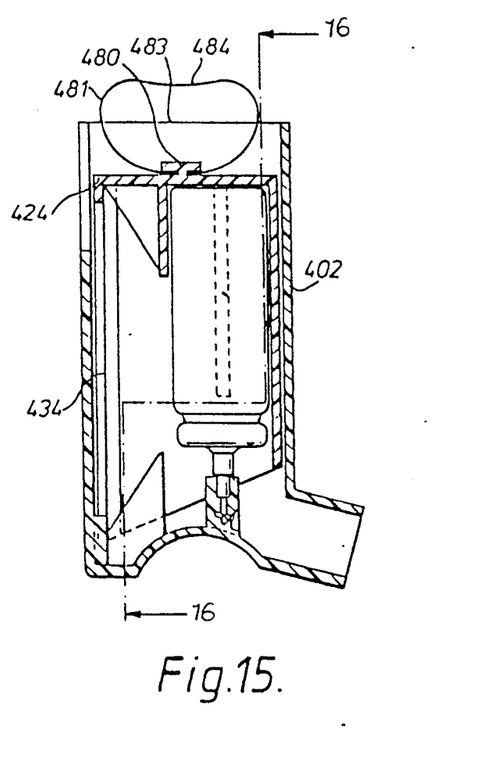
FIG. 15 shows a fifth embodiment of the invention and is a vertical section taken on line A—A in FIG. 16.
Figure 16:
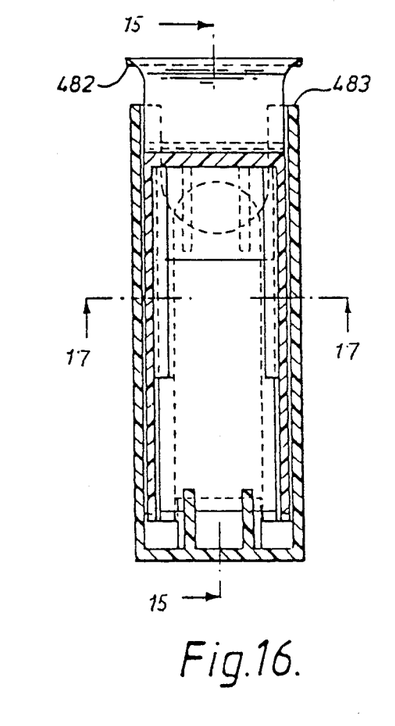
FIG. 16 is a section taken on line B—B in FIG. 15.
Figure 17:
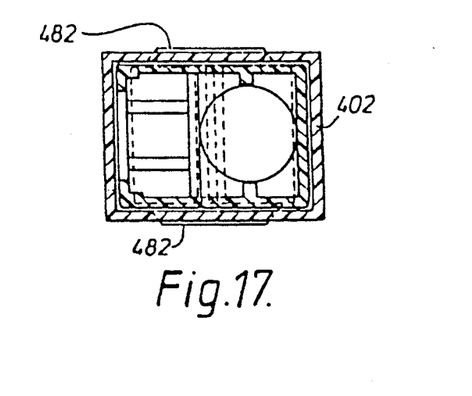
FIG. 17 is a cross-section taken on line C—C in FIG. 16.

The embodiment just described, although it has the advantage of simplicity, has the disadvantage that it requires a degree of skill on the part of the user to operate it. This is particularly so because the user needs to judge correctly the amount of force to apply. Too weak a force will fail to operate the device at all, and too strong a force may damage it. To mitigate this problem, the embodiment just described can be modified by providing it with a mechanism which limits the force which the user can transmit to the device. This fifth embodiment is shown in FIGS. 15 to 17. Apart from the force transmitting mechanism the elements of the fifth embodiment correspond substantially to those of the fourth embodiment, and elements in the fifth embodiment which correspond generally to elements in the fourth embodiment are denoted by the same reference numerals but with the addition of a further 100.

Figure 17A:
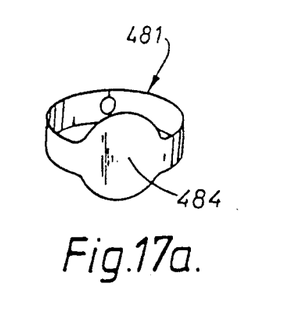
FIG. 17a is a perspective view of the resilient button used in FIGS. 15 to 17.

In the embodiment shown in FIGS. 15 to 17a the upper face of the guide 424 is provided with a fixing lug 480 to which is attached a resilient push button 481. The force applied by the user to this button is transmitted by the spring to the guide 424, and is limited to the correct value by the presence of shoulders 482 which hit ribs 483, which are upstanding from the upper end of the housing 402, when the user applies a sufficient force to the face 484 of the push button 481. In the illustrated embodiment the button 481 is formed of a strip of spring steel, as shown in FIG. 17a, but other components, for example a helical spring with an enlarged top for form a physical stop, could be used instead.

The use of a resilient push button in the embodiment of FIGS. 15 to 17a not only avoids the need for the user to judge the correct level of force to apply, but also makes it easier to achieve the necessary coordination. Thus, the user can press on the button 481 until it can be pressed no further, thereby storing energy in the resilient push button, and then, when ready, can inhale. Upon inhalation the energy stored in the push button then drives the guide downwardly, causing a dose to be discharged.

The sixth embodiment, shown in FIGS. 18 to 22, is an alternative modification of the fourth embodiment, the modification this time serving to render the device automatic to operation by equipping it with an energy storage device. Elements in the sixth embodiment which correspond generally to elements in the fourth embodiment are denoted by the same reference numerals but with the addition of a further 200.

Figure 18:
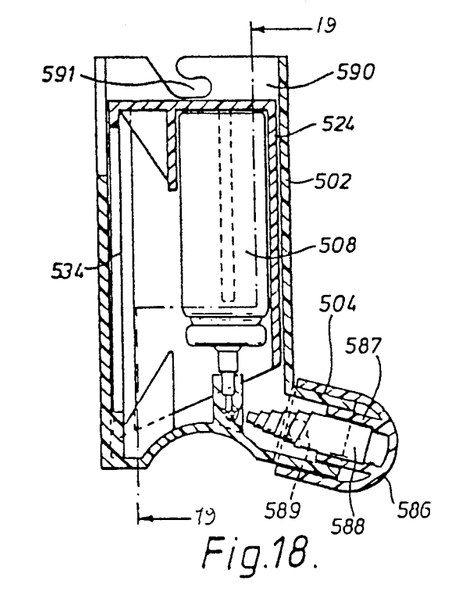
FIG. 18 shows a sixth embodiment of the invention and is a vertical section on line A—A in FIG. 19.
Figure 19:
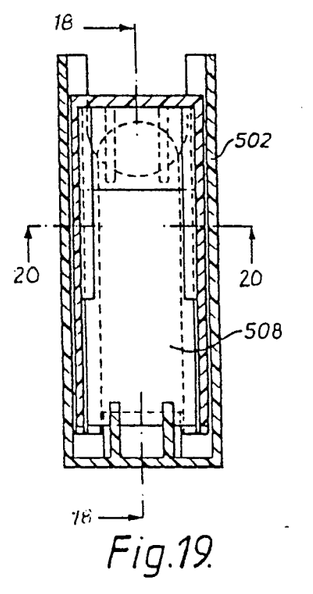
FIG. 19 is a section on line B—B in FIG. 18.
Figure 20:
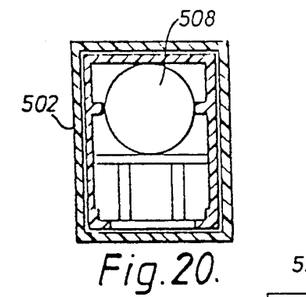
FIG. 20 is a cross-section on line C—C in FIG. 19.

The device shown in FIGS. 18 to 22 is provided with a mouthpiece cover 586 which, in the position shown in FIG. 18, fits over the mouthpiece 504. The cover 586 has an inner tubular sleeve 587 the end portion of which is received within the mouthpiece 504. An energy storage device in the form of a spiral spring 588 is mounted within the sleeve 587.

Figure 21:
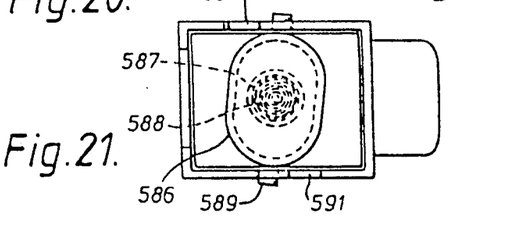
FIG. 21 is an top plan view of the sixth embodiment shown in its resetting position.
Figure 22:
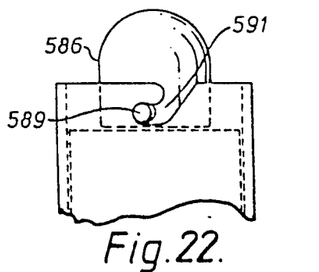
FIG. 22 is a partial side view of the sixth embodiment in the position shown in FIG. 21.

The cover 586 is provided with a pair of pins 589, and the upper end of the housing 502 is provided with a bayonet fitting 590 having notches 591 in which the pins 589 can be respectively received in order that the cover, after removal from the mouthpiece, can be mounted on the upper end of the device. FIGS. 21 and 22 show the cover 586 after it has been so mounted. The act of mounting the cover 586 in the bayonet fitting 590 causes the spiral spring 588 to be longitudinally compressed, and this results in the spring exerting a downward force on the guide 524. The spring 588 thus performs a function comparable to that of the springs 28 and 228 in the first and third embodiments.

Thus, in use, the patient removes the cover 586 and mounts it in the bayonet fitting 590 in order to bring the device into its cocked position. The patient then inhales to receive a dose of medicament, and thereafter removes the cover 586 from the bayonet fitting. This allows the guide 524, and hence the aerosol container body portion 508, to return to their original positions. The cover 586 is then re-mounted on the mouthpiece 504.

As already mentioned, the plates 34, 134, 234, 334, 434 and 534 may be made of a resiliently flexible metal, such as steel. However, other materials may be used instead, for example plastics and laminates of metals and plastics. The springs used in the various embodiments will normally be of metal, and the remaining components, apart from the aerosol container itself, may most suitably be made of a mouldable plastics material. All the aerosol containers used, even the non-conventional one used in the second embodiment, are of the type in which there is a metering chamber which automatically refills with a dose of liquid when the discharge stem moves outwardly with respect to the body portion of the container.

We claim:

1. An inhalation device for use with an aerosol container having a body portion and a discharge stem movable with respect to the body portion from a rest position in which discharge is prevented to an operative position in which discharge takes place, the device comprising a housing for the inhalation device, an outlet provided in the housing through which a patient can inhale, and a restraining and pressure-sensing member having a first position in which it prevents relative movement between the discharge stem and the body portion to the operative position and a second position in which is permits such movement, the said member sensing when a reduced pressure is produced through inhalation by the patient and moving from the first position to the second position in response thereto, said restraining and pressure-sensing member comprising a resiliently flexible plate, said plate extending between a first location fixed with respect to the housing and a second location fixed with respect to the body portion of the aerosol container, said plate bowing in passing from its first position to its second position or vice versa.

2. A device according to claim 1, comprising an energy store operable, on movement of the restraining and pressure-sensing member to its second position, to cause the said body portion and discharge stem to move with respect to one another to the said operative position.

3. A device according to claim 2, wherein the said energy store is a spring.

4. A device according to claim 3, wherein the discharge stem is received in a stem block fixed with respect to the housing, and the said body portion is longitudinally slidable within the housing to bring the body portion and discharge stem into and out of the said operative position, and wherein the said spring is a spring arranged to urge the housing towards the operative position.

5. A device according to claim 4, wherein the said body portion is mounted in, and movable with, a guide member, and the said spring acts between the said guide member and the housing or a member fixed with respect to the housing.

6. A device according to claim 4, wherein the said spring is provided with means enabling it to be removably mounted at a position in which it urges the housing towards the operative position.

7. A device according to claim 6, wherein the said spring is held in a cover member adapted to serve as a cover for the inhalation outlet when the spring and cover member are dismounted from the aforesaid position at which it urges the housing towards the operative position.

8. A device according to claim 3, wherein the discharge stem is received in a stem block fixed with respect to the housing, the said body portion is longitudinally slidable within the housing to bring the body portion and discharge stem into and out of the said operative position, the said spring is located within the said body portion and is arranged to bias the body portion and discharge stem with respect to one another towards the operative position, and means are provided for holding the discharge stem in the stem block against the biassing force of the spring.

9. A device according to claim 2, wherein the said energy store is in the form of a spring-loaded, manual actuation member, the actuation member being arranged to engage the housing when a force is exerted thereon in excess of a predetermined maximum, to prevent a force in excess of the said maximum being exerted between the said body portion and the said discharge member.

10. A device according to claim 1, wherein the plate is bowed in one direction when in its first position and in an opposite direction when in its second position, the plate passing through an intermediate, planar condition, in going from one position to the other.

11. A device according to claim 1, wherein the plate is substantially planar when in its first position and bowed when in its second position, the plate having a natural curvature in a direction opposite to that in which it bows in its second position, means being provided for preventing the plate, when in its first position, from assuming its natural curvature.

12. A device according to claim 1, comprising cocking means for returning the plate to its first position.

13. A device according to claim 12, wherein the cocking means comprises a cocking member movable by a user to cause it to engage the flexible plate and urge it to its first position.

14. A device according to claim 13, wherein the cocking member is a resiliently flexible tab forming part of a wall of the said housing.

15. A device according to claim 13, wherein the cocking member is a resiliently flexible membrane forming part of a wall of the said housing.

16. A device according to claim 13, wherein the said outlet is provided with a cover which has the cocking member thereon, an aperture being provided in a wall of the housing to enable the cocking member to pass therethrough into engagement with the flexible plate when the outlet is closed by the cover.

* * * * *

UNITED STATES PATENT AND TRADEMARK OFFICE
CERTIFICATE OF CORRECTION

PATENT NO. : 5,224,472
DATED : July 6, 1993
INVENTOR(S) : Yvan Pesenti et al.

It is certified that error appears in the above-indentified patent and that said Letters Patent is hereby corrected as shown below:

In Column 3, line 27, delete "a opening" and substitute therefor ---an opening---.

In Column 8, line 1, delete "for" and substitute therefor ---to---.

In Column 8, line 16, delete "to" and substitute therefor ---in---.

Signed and Sealed this

Twelfth Day of July, 1994

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

Page 1 of 2

PATENT NO. : 5,224,472
DATED : July 6, 1993
INVENTOR(S) : Yvan Pesenti, et. al.

It is certified that error appears in the above-indentified patent and that said Letters Patent is hereby corrected as shown below:

In Column 2, line 33, delete "A-A" and substitute therefor --1-1--.

In Column 2, line 35, delete "B-B" and substitute therefor --2-2--.

In Column 2, line 36, delete "C-C" and substitute therefor --3-3--.

In Column 2, line 39, delete "A-A" and substitute therefor --4-4--.

In Column 2, line 40, delete "B-B" and substitute therefor --5-5--.

In Column 2, line 42, delete "C-C" and substitute therefor --6-6--.

In Column 2, line 46, delete "A-A" and substitute therefor --8-8--.

In Column 2, line 47, delete "B-B" and substitute therefor --9-9--.

In Column 2, line 49, delete "C-C" and substitute therefor --10-10--.

In Column 2, line 52, delete "A-A" and substitute therefor --11-11--.

In Column 2, line 53, delete "B-B" and substitute therefor --12-12--.

In Column 2, line 54, delete "C-C" and substitute therefor --13-13--.

UNITED STATES PATENT AND TRADEMARK OFFICE
CERTIFICATE OF CORRECTION

PATENT NO. : 5,224,472
DATED : July 6, 1993
INVENTOR(S) : Yvan Pesenti, et. al.

It is certified that error appears in the above-indentified patent and that said Letters Patent is hereby corrected as shown below:

In Column 2, line 59, delete "A-A" and substitute therefor —15-15—.

In Column 2, line 60, delete "B-B" and substitute therefor —16-16—.

In Column 2, line 61, delete "C-C" and substitute therefor —17-17—.

In Column 2, line 66, delete "A-A" and substitute therefor —18-18—.

In Column 2, line 67, delete "B-B" and substitute therefor —19-19—.

In Column 2, line 68, delete "C-C" and substitute therefor —20-20—.

In Column 3, line 27, delete "a opening" and substitute therefor —an opening—.

In Column 8, line 1, delete "for" and substitute therefor —to—.

In Column 8, line 16, delete "to" and substitute therefor —in—.

Signed and Sealed this

Twenty-second Day of November, 1994

Attest:

BRUCE LEHMAN

Attesting Officer     Commissioner of Patents and Trademarks